United States Patent [19]

Benton

[11] Patent Number: 4,783,252
[45] Date of Patent: Nov. 8, 1988

[54] LATERAL INDICATOR SENSOR

[75] Inventor: Barry W. Benton, Orange, Calif.

[73] Assignee: Rosemount Inc., Eden Prairie, Minn.

[21] Appl. No.: 20,364

[22] Filed: Mar. 2, 1987

[51] Int. Cl.$^4$ ............................................. G01N 27/46
[52] U.S. Cl. ..................................... 204/416; 204/400; 204/409; 204/420; 204/435
[58] Field of Search ........................ 204/415, 416–420, 204/400, 409, 435

[56] References Cited

U.S. PATENT DOCUMENTS

| | | | |
|---|---|---|---|
| 2,563,062 | 8/1951 | Perley | 204/428 |
| 3,503,861 | 3/1970 | Volpe | 204/415 |
| 3,652,439 | 3/1972 | Ben-Yaakov et al. | 204/195 |
| 3,787,307 | 1/1974 | Schwab et al. | 204/420 |
| 3,829,761 | 8/1974 | Shimizu et al. | 324/30 B |
| 3,879,279 | 4/1975 | Baucke | 204/419 |
| 3,929,603 | 12/1975 | Porter | 204/195 P |
| 4,036,722 | 7/1977 | Brushwyler et al. | 204/195 B |
| 4,432,366 | 2/1984 | Margules | 204/415 |
| 4,447,309 | 5/1984 | Morioka et al. | 204/402 |
| 4,575,410 | 3/1986 | Neti | 204/422 |

OTHER PUBLICATIONS

Abstract of Pfaudler-Werke AG British Pat. GB 1596-117, *Scientific Instrumentation,* D34, p. 31.
"pH and ORP Systems", Bulletin 101, pp. 7–8, Control Data Corporation.
Brochure: "Die Neue Generation", Conducta Brochure.
Brochure: "Insertion/Submersion pH Sensor-Model PHS17", Elector–Chemical Devices, Inc.
Brochure: "pH/ORP Insertion Probe Mounting Assembly", Great Lakes Instruments, Inc.
Brochure: "Insertion Probe 768-35 and 769-35", Ingold Electronics Inc.
Brochure: "Model 520 Series pH/Redox Sensor-Transmitter", Lakewood Instruments, Inc.
Brochure: "7774 Removable Type pH Mounting for General Purpose and Sterilizable Meredian Electrodes", L & N Inc.
Brochure: "Insertion/Submersion pH Sensor-Model 916", Sensor Technology, Inc.
Brochure: "MK 319 Wet Tap Assembly", Signet Scientific, Inc.
Brochure: "pH/ORP Sensors", TBI, Inc.
Brochure: "Mark VII Insertion Sensors", Van London Company, Inc.
Brochure: "Insertable Flat Surface Combination pH Electrode", Sensorex, Inc. Bulletin 410.

*Primary Examiner*—T. Tung
*Attorney, Agent, or Firm*—Kinney & Lange

[57] ABSTRACT

An electrochemical sensor for measuring an electrochemical parameter such as pH in a flowing liquid has a housing with a lateral cutout or indentation. An indicator electrode and a reference junction extend into the indentation from opposite sides so that they are facing one another and are axially aligned along a common longitudinal axis which is generally perpendicular to the flow of liquid.

21 Claims, 4 Drawing Sheets

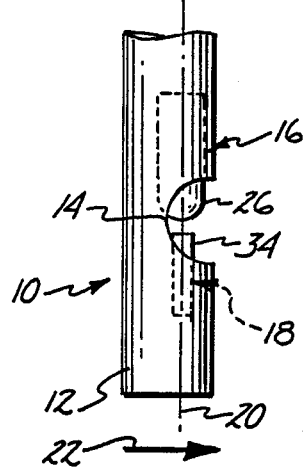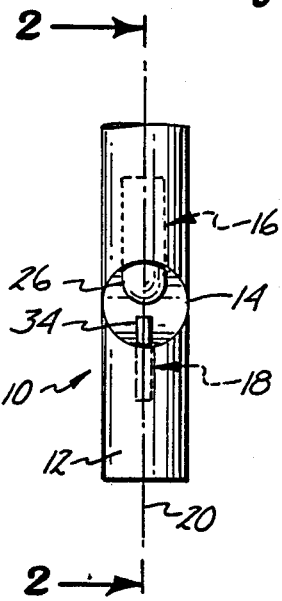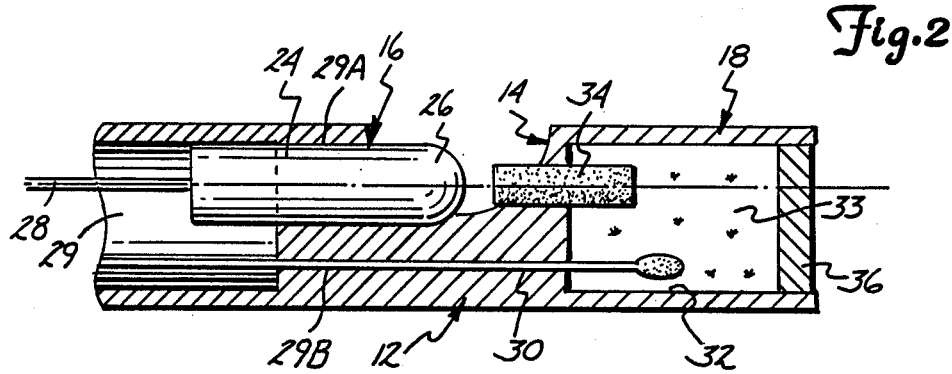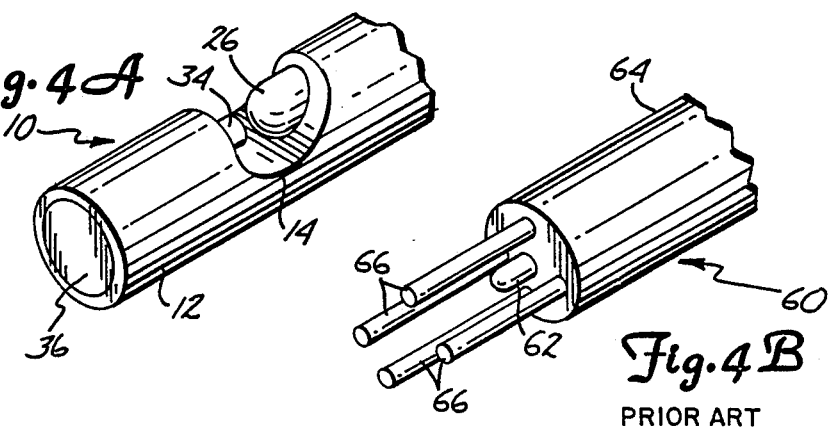

LATERAL INDICATOR SENSOR

BACKGROUND OF THE INVENTION

1. Field of the Invention

The invention relates to electrochemical sensors, and in particular to a sensor for measuring electrochemical activity of a selected species in a flowing material.

2. Description of the Prior Art

A wide variety of electrochemical sensors have been developed and used for industrial applications. For example, pH sensors have been used for many years and commonly make use of an indicator electrode and a reference electrode. The indicator electrode is commonly a pH sensitive glass member which contains a suitable electrolyte and in which is immersed an internal reference. The reference electrode commonly contains a reference solution (an electrolyte) and an internal reference. Unlike the indicator electrode, the reference electrode also includes some form of junction for establishing contact between its internal electrolyte and the liquid being tested. The sensor output signal is in the form of a potential between the indicator electrode and the reference electrode.

When this type of sensor is used to measure electrochemical activity in a flowing liquid, there are a number of potential sources of inaccuracies and problems which are encountered. In particular, streaming potentials caused by the flow of fluid past the indicator electrode and reference junction and stray electric current can both result in inaccurate potentials being produced. Sensors of this type have generally been rather fragile, and the insertion of the sensor through a sometimes obstructed passage into the fluid, and the possible presence of stream debris, can result in cracking or breaking of the indicator electrode. Fouling of the sensor by debris contained in the liquid stream also presents a problem with prior art electrodes.

SUMMARY OF THE INVENTION

The lateral indicator sensor of the present invention is an electrochemical sensor having an indicator electrode and a reference electrode which are supported by a housing in a relationship in which the active areas of the indicator electrode and reference electrode face one another and are closely spaced from one another. The housing has an indentation or cutout in a major side surface, and the active portions of the indicator electrode and reference electrode extend into the indentation from opposite sides so that they are closely spaced and axially aligned along a common longitudinal axis which is generally transverse to the direction of flow.

BRIEF DESCRIPTION OF THE DRAWINGS

FIGS. 1A and 1B are side and rear views, respectively, of a preferred embodiment of the lateral indicator sensor of the present invention.

FIG. 2 is a sectional view, along section 2—2 of FIG. 1B.

FIGS. 4A and 4B are perspective views of the lateral indicator sensor of the present invention and a prior art electrode with associated guard, respectively.

DETAILED DESCRIPTION OF THE PREFERRED EMBODIMENTS

Figure 3A:
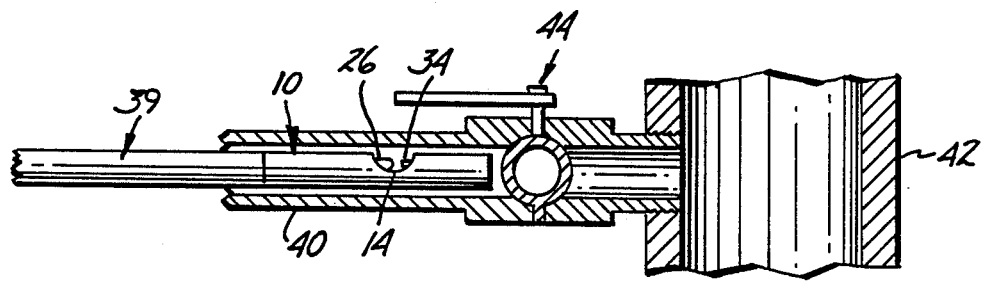
FIG. 3A shows the insertion of the lateral indicator sensor into a process pipe in which the passage for the sensor is blocked by a closed valve.

As illustrated in FIGS. 1A, 1B and 2, sensor 10 of the present invention has an elongated housing or body 12 with a lateral cutout or indentation 14. Projecting into indentation 14 from opposite directions are portions of indicator electrode 16 and reference electrode 18. Electrodes 16 and 18 are positioned along a common longitudinal axis 20 which is generally parallel to the longitudinal axis (not shown) of housing 12 and generally perpendicular to the direction of fluid or material flow, as indicated by arrow 22.

As best shown in FIG. 2, indicator electrode 16 is a generally cylindrical electrode, such as a pH sensing glass electrode having a main body 24 with an active region 26 at one end and a wire 28 extending from its opposite end. Indicator electrode 16 extends from main bore 29 of housing 12 through passage 29A so that active region 26 is positioned to be exposed to fluid within indentation or cutout 14.

Reference electrode 18 includes a reference wire 30 which extends through main bore 29 and passage 29B and into cavity 32. An electrolyte, such as a reference solution 33, fills cavity 32. Reference junction 34 has one end within cavity 32 and its opposite end extending into cutout region 14. Reference junction 34 is axially aligned with indicator electrode 16 and is positioned in close proximity to active area 26. Plug 36 closes cavity 32.

As liquid flows past sensor 10, some of the liquid contacts active area 26 and reference junction 34 within cutout region 14. Because of the ion selective characteristics of electrode 16, a potential difference is produced between indicator electrode wire 28 and reference wire 30. This potential, which is supplied to signal measuring circuitry (not shown), is a function of concentration of ions in the vicinity of active region 26 and reference junction 34.

As shown in FIG. 1A, the sensor 10 of the present invention is preferably positioned so that lateral cutout 14 is on the downstream side with respect to fluid flow. As a result, housing 12 partially shields active electrode 16 and reference electrode 18 from direct impingement of fluid and particles flowing in the direction designated by arrow 22.

The positioning of reference junction 34 and indicator electrode active region 26 along common longitudinal axis 20 creates a central current path between the two electrodes. The close proximity of active region 26 and the distal end of reference junction 34 provides a very short current path between reference electrode 18 and indicator electrode 16. Cutout region 14 ensures a stable current path with high electrolyte concentration in the proximity of indicator electrode 16 and reference electrode 18.

The proximity of active region 26 to reference junction 34 and their common longitudinal axis reduces the effect of streaming potentials. The common longitudinal axis 20 also reduces the effect of stream direction on sensor output. By locating lateral cutout 14 on the downstream side of sensor 10, high flow rate stream potentials are reduced because active region 26 and reference junction 34 are in a low flow rate area.

In prior art systems, in which the indicator and reference electrodes are not so closely spaced and aligned, stray current can produce a large potential difference error between the two electrodes. With the present invention, the proximity of active region 26 to reference junction 34, and their common longitudinal axis helps to reduce the potential errors caused by stray electrical current.

The proximity of active region 26 and reference junction 34 along common longitudinal axis 20 tends to minimize the resistance of the current path between the reference and indicator electrodes 18 and 16. As discussed previously, locating lateral cutout 14 on the downstream side of sensor 10 maximizes the concentration of reference electrolyte at the indicator electrode in the low flow rate area, thus reducing the current path resistance in high flow rate streams. This is particularly important when measuring pH in high purity water.

Figure 3B:
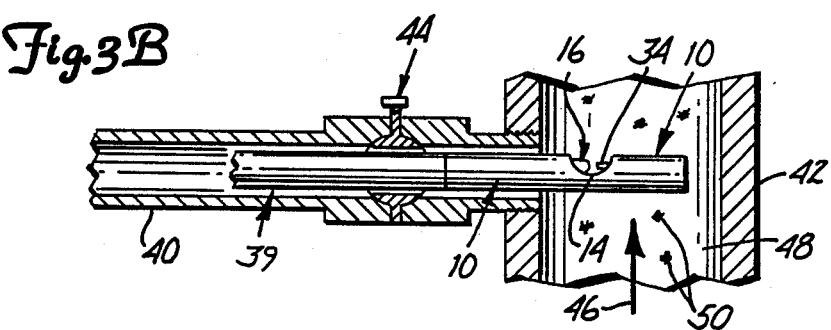
FIG. 3B shows the lateral indicator sensor in position in the process pipe, and shows the flow of liquid with debris in the process pipe.

Other important advantages of the sensor of the present invention are ilustrated in FIGS. 3A and 3B, where sensor 10 is a replaceable sensor cartridge mounted on the distal end of a probe insertion shaft 39. As shown in FIG. 3A, sensor 10 is being inserted through pipe 40 into process pipe 42. During insertion, sensor 10 will encounter an obstruction (in this case closed ball valve 44). Unlike prior art sensors in which the indicator electrode is mounted at the end of the sensor, the present invention ensures that the point of impact between sensor 10 and the obstruction is at a location away from indicator electrode 16 and particularly its active area 26. By locating active region 26 and reference junction 34 in lateral cutout 14, sensor 10 guards indicator electrode 16 from damage or breakage due to mishandling, obstructed insertion, or debris contained in the process flow.

FIG. 3B shows sensor 10 inserted through pipe 40 and open ball valve 44 into process pipe 42. The direction of flow, as indicated by arrow 46 in FIG. 3B, carries the liquid 48 and debris 50 past the distal end of sensor 10. By locating lateral cutout 14 on the downstream side, housing 12 protects indicator electrode from damage caused by flowing debris 50.

FIGS. 4A and 4B illustrate another important advantage of the present invention. FIG. 4A is a perspective view of sensor 10, while FIG. 4B illustrates a prior art sensor 60. As shown in FIG. 4B, sensor 60 includes an indicator electrode 62 carried by housing 64. At the distal end of housing 64 are a plurality of posts 66 which form a guard around the active area of indicator electrode 62. Guard posts 66 protect the active regions of electrode 62 against damage, particularly in the case of an obstructed insertion like that illustrated in FIG. 3A.

The disadvantage of the prior art sensor 60 as illustrated in FIG. 4B is that the guard posts 66 project out from body 64. As a result, they provide projections on which fibrous material carried in the process liquid can be tangled or caught. As a result, guard posts 66 can accumulate material which eventually fouls sensor 60.

With sensor 10 of the present invention, on the other hand, active region 26 of indicator electrode 16 is protected by being positioned within lateral cutout 14. No projections are required in order to provide protection against mishandling or damage caused by obstructions during insertion, and therefore there are no projections to interrupt free flow. This reduces the tendency of fouling caused by process stream debris.

Figure 5A:
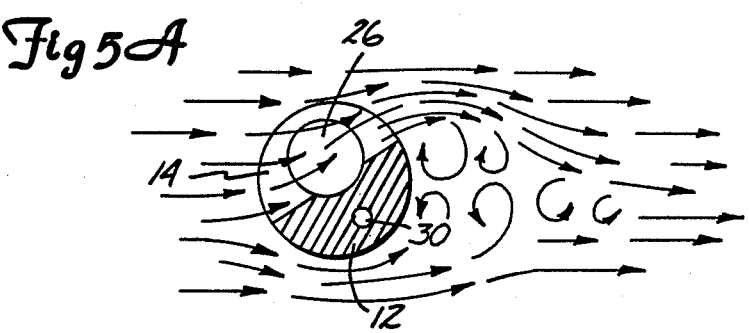
FIG. 5A and 5B show flow of liquid past the indicator electrode with two different orientations of the lateral indicator sensor with respect to the liquid flow direction.
Figure 5B:
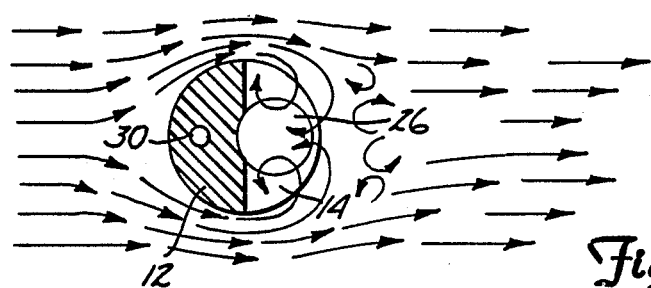

Another advantage of the sensor 10 of the present invention is that by rotating sensor 10 the orientation of cutout region 14 and electrodes 16 and 18 with respect to the process stream can be changed. FIGS. 5A and 5B illustrate two different orientations of lateral cutout 14 which result in different fluid flow patterns past active region 26 of indicator electrode 16. In FIG. 5A, lateral cutout 14 has been rotated so that it is at least partially facing upstream. This results in an increased flow rate past active region 26 of indicator electrode 16. This increase in flow rate can be used to provide a scouring action.

In FIG. 5B, lateral cutout 14 is positioned on the downstream side of flow, so that sensor housing 12 acts as a bluff body to produce vortices and turbulent flow around active region 26. This can also be used to reduce the undesired precipitation in active region 26.

One problem encountered with electrochemical sensors having a reference which includes a reference junction is that changes in the pressure of the liquid being sensed relative to the reference solution can cause a loss of reference solution through the reference junction, or the migration in and contamination of the reference solution by the liquid being tested. FIGS. 6-9 illustrate four different embodiments of the reference electrode 18 of sensor 10 which are concerned with shifting junction potentials and loss of reference solution due to fluctuating stream pressure. In each of FIGS. 6-9, similar elements from FIGS. 1A, 1B and 2 are designated with similar reference numerals.

Figure 6:
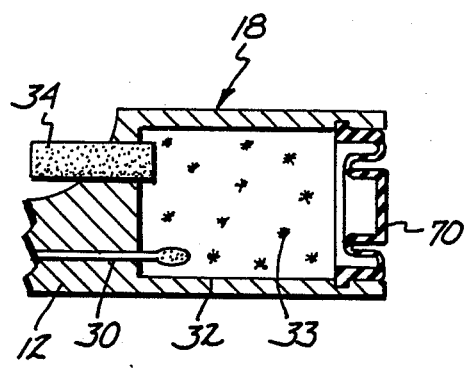
FIGS. 6–9 show other embodiments of the reference electrode of the lateral indicator sensor of the present invention.

In FIG. 6, plug 36 shown in FIG. 2 has been replaced by a flexible diaphragm 70. Diaphragm 70 is exposed to the external fluid pressure and transmits that fluid pressure to reference solution 33. Reference junction 34 is also exposed to the stream fluid pressure, so that the internal and external pressures across reference junction 34 are equalized. This eliminates reference solution loss which would otherwise be caused by a pressure differential.

Figure 7:
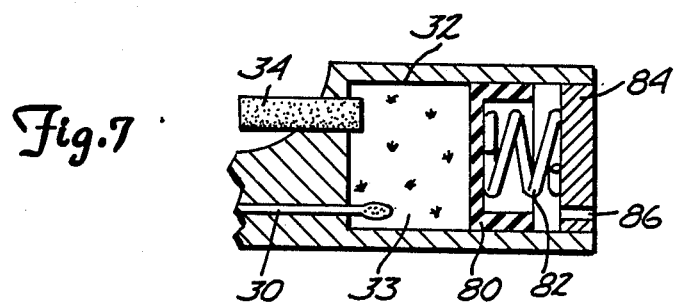

In FIG. 7, plug 36 has been replaced by plunger 80, spring 82 and plug 84 (which has a vent 86). In the embodiment shown in FIG. 7, therefore, force is being applied to reference solution 33 by an energized plunger 80 to maintain reference solution pressure above stream pressure. This ensures a consistent junction solution and concentration. Plunger 80 is energized by bias spring 82 (which is partially under compression) and by fluid pressure of the stream, which is transmitted to the backside of plunger 80 through vent 86.

Figure 8:
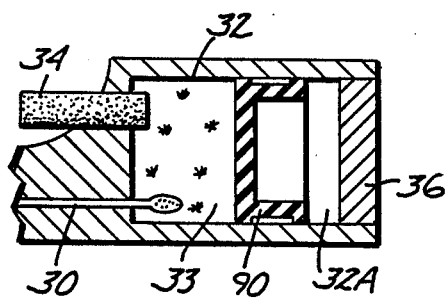

FIG. 8 shows another embodiment in which plunger 90 is located within chamber 32. A high pressure gas fills the portion of cavity 32A between the back side of plunger 90 and plug 36. This gas pressure is at a pressure which is higher than the stream fluid pressure. The result is that reference solution 33 is maintained under a consistent pressure, but one which is not relative to stream pressure.

Figure 9:
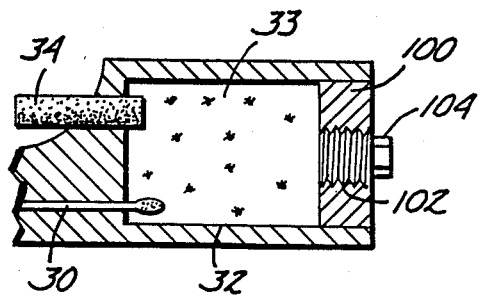

FIG. 9 shows still another embodiment in which plug 100 at one end of cavity 32 contains a threaded passage 102 in which removable plug 104 is threaded. Cavity 32 can be refilled with reference solution by removing plug 104 from passage 102.

Figure 10A:
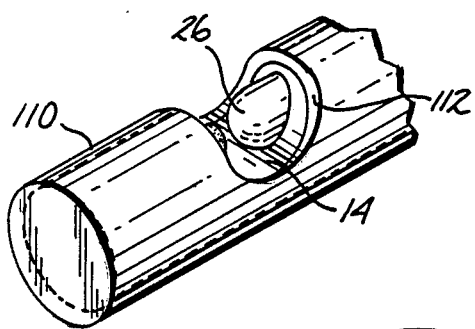
FIGS. 10A and 10B are perspective views showing the lateral indicator sensor of the present invention in conjunction with an outer housing or sheath.
Figure 10B:
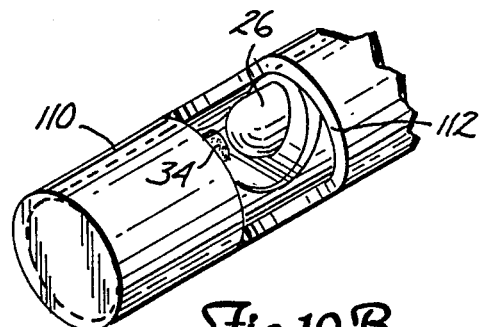

FIGS. 10A and 10B show another embodiment of the present invention, in which variable guarding of active area 26 of indicator electrode 16 is provided. In this embodiment, an outer housing or shroud 110 is positioned over housing 12 of sensor 10. Shroud 110 has a lateral cutout 112 which is positionable with respect to lateral cutout 14 by relative movement of housing 12 and shroud 110.

In FIG. 10B, shroud cutout 112 has been rotated 90° with respect to sensor lateral cutout 14. A greater amount of guarding of electrode active area 26 can be achieved by rotating shroud 112 in the counterclockwise direction shown in FIG. 10B relative to housing 12. Conversely, a lesser extent of guarding can be achieved by rotating shroud 110 in a clockwise direction relative to housing 12.

Although cutout 112 illustrated in FIGS. 10A and 10B is of the same general configuration as lateral cutout 14, in other embodiments the configuration of cutout 112 and cutout 14 can be different to enhance the guarding action.

Still another advantage which can be achieved is electrical shielding from stray currents in the process fluid by shroud 110. This requires that shroud 110 be an electrically conductive material.

Figure 11:
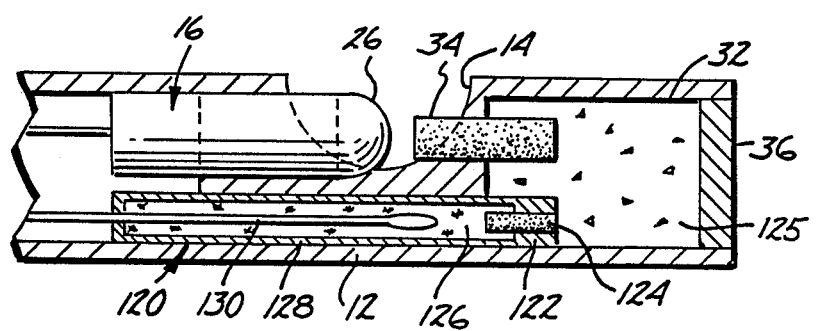
FIG. 11 shows another embodiment of the lateral indicator sensor of the present invention having a double junction reference electrode.

FIG. 11 shows another embodiment of sensor 10 in which reference wire 30 has been replaced with another reference electrode 120 to produce a double junction reference electrode. Reference electrode 120 includes a housing 122 having a junction 124 at one end which is exposed to the interior of cavity 32 and thus to electrolyte solution 125. The opposite end of junction 124 is exposed to second reference solution 126 in cavity 128 of housing 122. Reference wire 130 has one end located within cavity 128 and its opposite end extending out to provide electrical connection to sensing circuitry (not shown).

Although the present invention has been described with reference to preferred embodiments, workers skilled in the art will recognize that changes may be made in form and detail without departing from the spirit and scope of the invention. For example, although the present invention is ideally suited to glass pH electrodes, it is also applicable to other sensors using different indicator electrodes, such as glass ion-selective electrodes, solid state ion-selective or pH electrodes, and indicator electrodes using permeable or semi-permeable membranes. Similarly, other reference electrodes, including those using a solid electrolyte, can also be used.

What is claimed is:

1. A sensor for sensing an electrochemical parameter of a flowing process material and providing an output representative of the parameter, the sensor comprising:
   a sensor body having an indentation forming an indentation surface recessed from a side surface of the sensor body which opens to receive a portion of the process material; and
   a plurality of electrodes extending from the indentation surface into the indentation to form a plurality of electrode surfaces spaced away from the indentation surface for contacting the process material in the indentation.

2. The sensor of claim 1 wherein the sensor body has the side surface disposed to face downstream in the flowing process material; and wherein the indentation opens downstream such that the body shields the electrodes from suspended particles in the flowing process material.

3. The sensor of claim 1 wherein the sensor body has the side surface disposed to face upstream in the flowing process material and the indentation opens upstream such that the electrodes receive an increased flow of the process material for cleaning the electrodes.

4. The sensor of claim 1 wherein the sensor body comprises an elongated probe for extending into a region of flowing process material.

5. The sensor of claim 4 wherein a first electrode of the plurality of electrodes comprises a reference junction electrode.

6. The sensor of claim 5 wherein a second electrode of the plurality of electrodes comprises a species selective electrode.

7. The sensor of claim 6 wherein the species selective electrode is pH sensitive.

8. The sensor of claim 4 wherein the side surface of the probe is substantially cylindrical for insertion through a ball valve into the flowing process material.

9. A sensor probe insertable into a flowing process material, the sensor probe comprising:
   a probe body having a distal end for insertion in the flowing process material, a proximal end disposed away from the distal end and connected by a side wall having an indentation forming an indentation surface therein which is spaced away from the distal end;
   first electrode means disposed in the probe body and extending outwardly from the indentation surface into the indentation; and
   second electrode means spaced away from the first electrode means and having a reservoir of electrolyte in the probe body and junction means permeable to the electrolyte coupled between the reservoir and the indentation for electrochemically coupling to the process material, the junction means protruding into the indentation.

10. The probe of claim 9 wherein the first electrode means has an active region disposed opposite the junction means in the indentation.

11. The probe of claim 9 further comprising means coupled to the reservoir for controlling pressure of the electrolyte.

12. The probe of claim 11 wherein the means for controlling pressure comprise a diaphragm disposed in the probe body for coupling pressure from the process material to the electrolyte.

13. The probe of claim 11 wherein the means for controlling pressure comprise means disposed in the probe body for producing a force and a plunger for transferring the force to the electrolyte.

14. The probe of claim 13 wherein the means for producing a force comprise a coil spring.

15. The probe of claim 13 wherein the means for producing a force comprise compressed gas.

16. The probe of claim 9 further comprising a shroud positioned on the side wall and having an aperture therethrough which is positionable with respect to the indentation for controlling exposure of the first and second electrode means to the process material.

17. A sensor comprising:

an elongated housing having a lateral cutout in a side wall;

indicator electrode means supported by the housing and having an active region protruding into the cutout; and reference electrode means supported by the housing and having an active region protruding into the cutout opposite and spaced from the indicator electrode active regions, the active regions being essentially aligned along a common longitudinal axis which is generally parallel to an elongated direction of the housing.

18. The sensor of claim 17 wherein the housing has a cavity therein; and wherein the reference electrode means includes an electrolyte within the cavity, and means for providing electrochemical contact with the electrolyte.

19. The sensor of claim 18 wherein the means for providing electrochemical contact includes a reference wire, a reference solution, and a permeable junction extending between the reference solution and the electrolyte.

20. The sensor of claim 17 wherein the housing has a main bore and a passage extending between the main bore and the cutout; and wherein the indicator electrode means extends from the main bore through the passage into the cutout.

21. The sensor of claim 17 and further comprising a shroud mounted over and movable with respect to the housing, the shroud having an aperture which is positionable with respect to the cutout by relative movement between the shroud and the housing.

* * * * *